Figure 1:
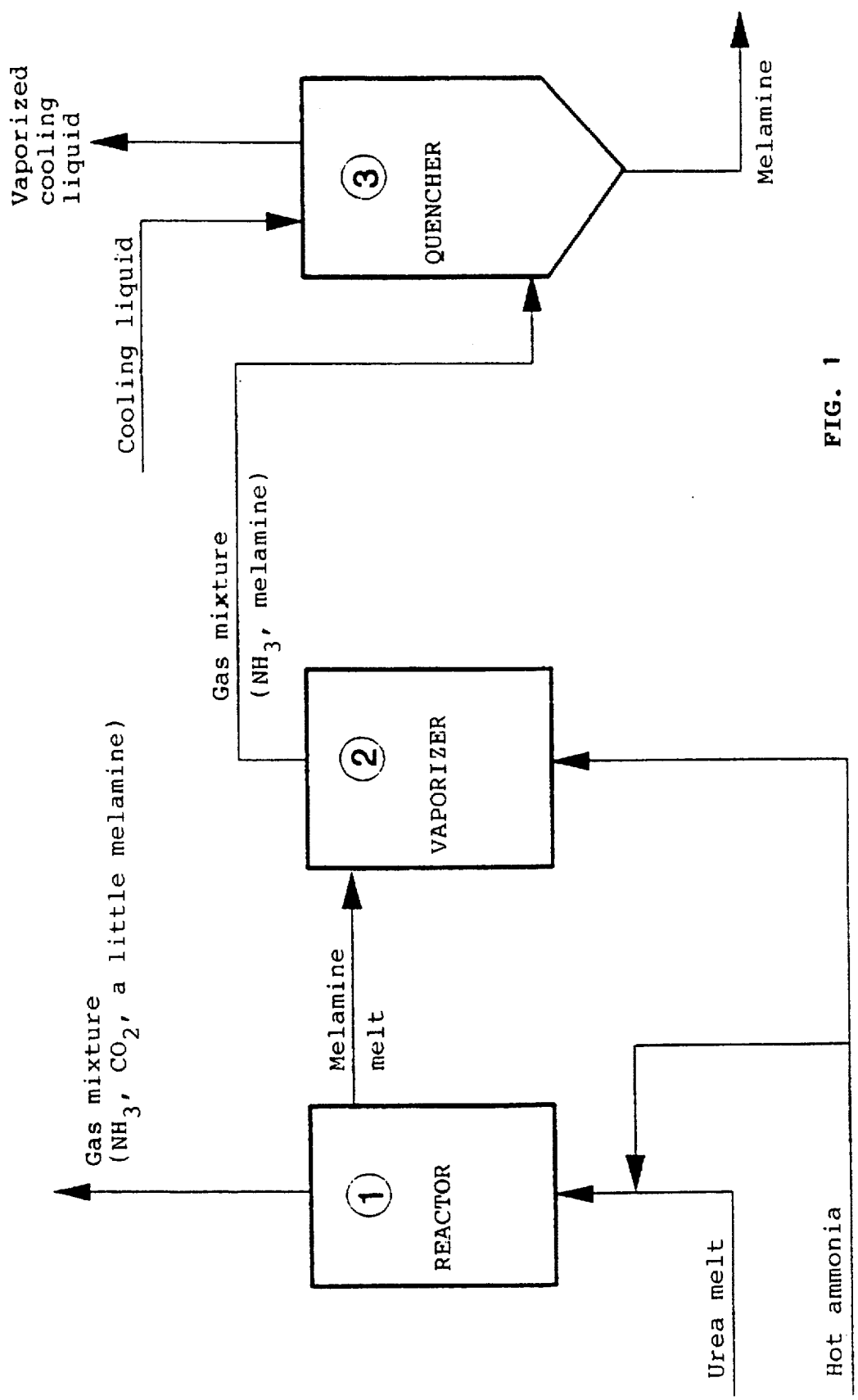

United States Patent [19]

Turunen et al.

[11] Patent Number: 5,731,437
[45] Date of Patent: Mar. 24, 1998

[54] PROCESS FOR THE PREPARATION OF MELAMINE

[75] Inventors: Ilkka Turunen, Oulu; Pekka Oinas, Kokkola, both of Finland

[73] Assignee: Kemira Agro Oy, Finland

[21] Appl. No.: 571,929

[22] PCT Filed: Jul. 1, 1994

[86] PCT No.: PCT/FI94/00307

§ 371 Date: Jun. 13, 1996

§ 102(e) Date: Jun. 13, 1996

[87] PCT Pub. No.: WO95/01345

PCT Pub. Date: Jan. 12, 1995

[30] Foreign Application Priority Data

Jul. 1, 1993 [FI] Finland ................... 933033

[51] Int. Cl.$^6$ ............ C07D 251/60; C07D 251/62
[52] U.S. Cl. ................... 544/201; 544/203
[58] Field of Search ................... 544/201, 203

[56] References Cited

U.S. PATENT DOCUMENTS

| | | | |
|---|---|---|---|
| 3,484,440 | 12/1969 | Kokubo et al. | 260/249.7 |
| 4,565,867 | 1/1986 | Thomas et al. | 544/201 |
| 5,514,797 | 5/1996 | Best | 544/203 |

FOREIGN PATENT DOCUMENTS 0 612 560 A1  8/1994  European Pat. Off. .

800722  9/1958  United Kingdom .

OTHER PUBLICATIONS

Shiroishi et al., "Technical Development of Melamine Manufacture by Urea Process", *Chemical Economy & Engineering Review*, vol. 8, No. 1, 2 (No. 92), pp. 34–39, 46, 47, 50, 51 (Jan. & Feb. 1976).

Ellwood, "Melamine Process Uses Low–Pressure Reactor to Achieve Low Costs", *Chemical Engineering*, pp. 124–126 (May 20, 1968).

Schwarzmann, "Make Melamine at Atmospheric Pressure", *Hydrocarbon Processing*, pp. 184–186 (Sep. 1969).

Schmidt, "New OSW Process Makes Melamine", *Hydrocarbon Processing*, vol. 45, No. 11, pp. 146–150 (Nov. 1966).

*Primary Examiner*—John M. Ford
*Attorney, Agent, or Firm*—Nath & Associates; Gary M. Nath; Suet M. Chong

[57] ABSTRACT

The invention relates to a process for the preparation of melamine from urea by feeding molten urea and hot ammonia gas into a reactor having a pressure within the range 50–150 bar and a temperature within the range 360°–430° C., whereby a reaction product is obtained which contains a liquid melamine melt and a gas mixture. This gas mixture is separated from the liquid melamine melt, and the liquid melamine melt thus obtained is directed to a vaporizer and is vaporized therein, and the melamine-containing gas obtained from the vaporizer is cooled in a quencher, in which case the melamine crystallizes in a very pure state, the purity being typically at minimum 99.9%.

18 Claims, 4 Drawing Sheets

PROCESS FOR THE PREPARATION OF MELAMINE

This application is a 371 of PCT/FI94/00307, filed Jul. 1, 1994.

The present invention relates to the preparation of melamine from urea. More precisely, the invention relates to the preparation of very pure melamine by a new high-pressure process.

It is known that melamine can be prepared from urea at a temperature of 390°–410° C. according to the following reaction formula:

$$6H_2N\text{—}CO\text{—}NH_2 \rightarrow C_3N_3(NH_2)_3 + 6NH_3 + 3CO_2$$

The reaction is strongly endothermic. The heat requirement is 649 kJ per melamine mole, when the heating of the urea from 135° C. (melting point of urea) to the reaction temperature is included.

Users require a very high purity of melamine; 99.8% and 99.9% are typical degrees of purity in product specifications. For this reason its production processes often include a complicated purification section involving a large quantity of apparatus.

There are two basic types of melamine production processes using urea as the raw material, namely, catalytic low-pressure processes and high-pressure processes in which no catalyst is used. In the former, the reactor pressure is approx. 10 bar or lower, in the latter higher than 80 bar (Ullmann's Encyclopedia of Industrial Chemistry, 5th edition, Vol. A 16, p. 174).

In typical low-pressure processes, a fluid-bed reactor is used in which the catalyst is fluidized with gaseous ammonia or a mixture of ammonia and carbon dioxide. The melamine emerges in gaseous state from the reactor. The fact that corrosion is less than in high-pressure processes is regarded as one of the advantages of low-pressure processes. The best known users of low-pressure processes are BASF (Hydrocarbon Processing, September 1969, p. 184), Chemie Linz (Hydrocarbon Processing, November 1966, p. 146), and DSM/Stamicarbon (Chem. Eng., May 20, 1968, p. 124), each of which has developed its own process version.

In typical high-pressure processes the reaction takes place in a liquid phase. In this case the reactor is full of molten melamine mixed to some degree with molten raw material, i.e. urea, and intermediate reaction products. Also present in the mixture there are gas bubbles consisting of ammonia and carbon dioxide and a small amount of gaseous melamine. The required high amount of reaction heat is usually generated by intra-reactor heating elements, in which the heat is generated by means of electricity or, for example, a circulating hot salt melt.

Smaller apparatus size can be deemed to be one of the advantages of high-pressure processes over low-pressure processes. A reaction taking place in a liquid phase clearly requires less space. Furthermore, the process apparatus in which gas is treated remain moderate-sized owing to the high pressure. Another advantage is the high pressure of the obtained the product gas, a mixture of ammonia and carbon dioxide. This gas is often used for the preparation of urea and, being pressurized, it is better suited for this purpose as such.

The Montedison process (Ausind) is a typical high-pressure melamine production process (Ullmann's Encyclopedia of Industrial Chemistry, 5th edition, Vol. A 16, p. 177). As in other melamine processes, urea melt and hot ammonia are introduced into a reactor. The reactor conditions are 70 bar and 370° C. From the reactor the mixture of melamine melt and product gases is directed to a quencher, into which water containing ammonia and carbon oxide is also introduced. The temperature of the quencher is 160° C. and its pressure 25 bar. From this quencher the reactor offgases are fed for further use, for example for the production of urea or fertilizers. The melamine is recovered from the slurry by a highly multiple-stage further treatment, which includes the removal of ammonia and carbon dioxide, the dissolving of the melamine in a large amount alkaline water, removal of color with activated carbon, crystallization, filtration, drying, and packaging.

The Montedison process has two significant disadvantages which the present invention does not have, for example, the product gas is obtained at a relatively low pressure, only 25 bar. Second, the number of process stages is very high, since the impure product obtained from the reactor requires a thorough purification treatment. Furthermore, the purification apparatus is relatively large in size, since the pressures in it are already low.

In the Nissan high-pressure process (Chemical Economy & Engineering Review, Vol. 8, (1976), No. 1, 2, p. 35), advantages have been gained over the Montedison process at least with respect to the offgases, as is evident from the following. Also in the Nissan process, melamine melt and hot ammonia are fed into the reactor. The temperature and the pressure are 400° C. and 100 bar. In the upper section of the reactor, the melamine Melt and the gases are separated. The gases are directed into a scrubbing tower, in which they are scrubbed with urea melt. The melamine present in the gas dissolves in the urea melt. At the same time the gases cool to approx. 200° C. The product gas is thus obtained at a pressure of 100 bar and in anhydrous state, which may be a considerable advantage in terms of its further use. The urea melt to be used as raw material is fed in via the scrubbing tower. There is heats up and water is removed from it (reacts with urea). The melamine melt is dissolved in an aqueous ammonia solution. This solution is maintained under ammoniacal pressure at 180° C. for a certain period, during which the impurities are said to be eliminated. Thereafter follows a further treatment with numerous apparatus, including filtration and crystallization. In comparison with the present invention, the number of unit operations and apparatus is really high, which raises the process costs.

Melamine Chemicals has developed a process (U.S. Pat. No. 4,565,867) in which the quantity of apparatus is quite small as compared with the Montedison and Nissan processes. The reactor, into which urea melt and hot ammonia are fed, operates at a temperature of 370°–425° C. and under a pressure of 110–150 bar. The mixture of melamine melt and product gases is fed into a gas separation tank, in which the product gases are separated. The gas separation tank operates under the same conditions as the reactor. After a scrub with urea, the product gases are directed for further use. As in the Nissan process, the product gases are obtained at a pressure of approximately 100 bar and in anhydrous state. As in the Nissan process, the urea melt is fed into the reactor via the urea scrubber. From the gas-separation tank the melamine melt is directed to a quencher unit, in which it is cooled rapidly by means of, for example, liquid ammonia or water. Crystalline melamine is obtained, which is withdrawn via the bottom of the quencher unit and taken to drying. There are no actual purification stages. The quantity of apparatus in the process is really small as compared with the processes described above. However, the purity of the product is only 96–99.5%. In this respect the process is not competitive with the processes described above, any more than with the process according to the present invention to be described below. Achieving a competitive purity by the Melamine Chemicals process would require that a purification process, for example one similar to those in any of the above processes, be installed after the process. Thereby the advantages of the process, i.e. small quantity of apparatus and consequent cost efficiency, would be eliminated.

In the process according to the invention now introduced, the quantity of apparatus is substantially the same as in the Melamine Chemicals process, but the purity of the product is in the order of 99.9%. This fully competitive purity is achieved by first vaporizing the melamine melt obtained from the reactor and by then crystallizing it out from the gas phase.

Purification of the product by vaporization has been proposed even previously. One of the earliest melamine preparation patents (GB Patent 800 771) includes an example in which approx. 9 kg of ammonia per one kilogram of melamine product is fed into a reactor which operates at the temperature of 400° C. and under a pressure of 40–80 bar. The amount of ammonia is in this case so high that all of the produced melamine is vaporized into the gas phase. The promoting effect of ammonia on melamine vaporization is based on the fact that it reduces the partial pressure of melamine in the gas phase. When the reaction equation presented in the foregoing and the additional ammonia are taken into account, a stoichiometric calculation shows that the composition of the gas leaving the reactor will be, in per cent by volume: ammonia 94.8%, carbon dioxide 3.9%, and melamine 1.3%. Thus the melamine has to be recovered from a very large amount of gas. Furthermore, before the large amount of ammonia can be recycled into the reactor for reuse, carbon dioxide has to be separated from it. Quite pure melamine could probably be produced by a process such as this. Indeed, the said patent states that the only impurity present in the product was unreacted urea. However, the process is uneconomical owing to the large gas amounts and the related separation operations, which are the separation of the melamine from a very large amount of gas and the separation of the carbon dioxide from a very large amount of ammonia.

In the process described above, the ammonia amount required could be decreased by lowering the reactor pressure or by raising the temperature. In this case the melamine would vaporize more easily into the gas phase, and ammonia would not be needed in such a large amount to lower its partial pressure. If the reactor pressure is lowered to below 50 bar, there will form in the reactor a solid which will complicate and ultimately hinder the operation of the reactor. This has been noted in, for example, patent U.S. Pat. No. 3,484,440, column 1, line 65. Raising the temperature to above 400° C. for its part increases corrosion and weakens the structural materials of the reactor.

Nissan has investigated a process (U.S. Pat. No. 3,484,440) which resembles that described above but can be managed with a smaller amount of ammonia, in which case the melamine content is many times higher in the offgas. In this process, hot ammonia is fed into the reactor at a rate of 0.2–1.0 g per each gram of urea. The reactor conditions are 360°–400° C. and 50–150 bar. From the reactor the liquid melamine melt and in its midst the product gases (ammonia and carbon dioxide) are directed via a heater into a vaporizer. A pressure of 40–100 bar and a temperature of 420°–480° C. are maintained in the vaporizer. When the pressure and the temperature are selected suitably within these limits, all of the melamine can be caused to vaporize into the gas phase. For example, when ammonia is fed into the reactor at a rate of 0.2 g per one gram of urea, the concentration of melamine in the leaving gas phase will be approx. 7% by volume, calculated stoichiometrically. When the feed of ammonia is 1 g per one gram of urea, the melamine content in the gas will be approx. 3.2% by volume. For example, the first-mentioned case (melamine 7% by volume) requires a pressure of approx. 72 bar and a temperature of 480° C. or, for example, a pressure of 40 bar and a temperature of 455° C. These pressure and temperature values were taken from a diagram in the patent. Before vaporization, however, the melamine is allowed to remain in the vaporizer in the form of a liquid melt for at minimum one hour. Thus the impurities formed in the reaction are caused to reconvert into melamine. From the vaporizer the melamine is directed to a separator, in which it is cooled with water, and will crystallize, the temperature being 150° C. and the pressure approximately atmospheric. In the patent text it is stated that the purity of the product thus obtained is 99%, and the purity obtained in the example in the patent is 99.2%. A product such as this is not competitive in terms of purity. Users require a 99.9% purity of melamine so commonly that this requirement is mentioned in a well-known handbook in the field (Ullmann's Encyclopedia of Industrial Chemistry, 5th edition, Vol. A 16, p. 179). Achieving this purity by the process last described would require a separate purification process, for example dissolving and recrystallization, as do most melamine processes. This would be an expensive addition and would make the entire sense of the vaporization questionable; indeed, purification could be started directly on the product obtained in molten state from the reactor, without wasting energy on vaporization.

In a comparison of the prior-art melamine production processes with the present invention, the processes can be divided into two categories. In most low-pressure processes and the Nissan (meaning the first-mentioned of the two Nissan processes referred to) and Montedison high-pressure processes, evidently a competitive purity is achieved, but the processes involve a multiple-stage purification section with a large quantity of apparatus, which clearly increases both the operating costs and the investment. The processes described in patents U.S. Pat. No. 4,565,867 and U.S. Pat. No. 3,484,440 constitute the second category. They are in the same category in terms of the quantity of apparatus, and they do not have the multiple-stage purification section mentioned above. However, the purity of the product obtained from them is not competitive.

Now a process has been invented in which a competitive purity (99.9% melamine) is achieved and which does not include a multiple-stage purification section as do, for example, the Montedison and Nissan (the first-mentioned) high-pressure processes. In terms of its size and the quantity of apparatus, the present new process is comparable to those disclosed in U.S. Pat. No. 4,565,867 and U.S. Pat. No. 3,484,440.

The invention thus relates to a process for the preparation of melamine from urea by feeding urea melt and hot ammonia gas into a reactor in which the pressure is within the range 50–150 bar and the temperature within the range 360°–430° C., whereby a reaction product is obtained which contains a liquid melamine melt and a gas mixture, the process being characterized in that the said gas mixture is separated from the liquid melamine melt and that the liquid melamine melt thus obtained is directed to a vaporizer and is vaporized therein, and that the melamine-containing gas obtained from the vaporizer is cooled, whereupon the melamine crystallizes in a pure state.

In the process according to the invention, the melamine crystallizes in so pure a state that additional purification is not needed. The purity is in this case advantageously at minimum 99.9%.

In the process according to the invention the melamine may be vaporized in the vaporizer by reducing the pressure or by increasing the temperature or by feeding ammonia gas into the vaporizer or by using two or all the three of these methods.

The melamine retention time in the vaporizer is preferably less than half an hour, and especially preferably less than 10 minutes.

According to one preferred embodiment, the cooling of the melamine-containing gas is carried out by contacting it directly with a liquid cooling agent, the temperature being less than 130° C. and the pressure less than 40 bar. The said cooling agent is preferably ammonia or water.

In the process according to the invention, the gas produced in the reactor is separated from the liquid melamine melt in the upper section of the reactor. Only the melamine melt is fed into the vaporizer. From this follows a substantial difference as compared with the above-mentioned processes in which the melamine is also vaporized. In the process according to the invention, carbon dioxide will not enter the vaporizer, since it is carried in the reactor offgas. To be exact, a very small amount of carbon dioxide, dissolved in the melamine melt, does pass into the vaporizer. However, this amount is so small that it is without significance. In the vaporizer the melamine is preferably vaporized by raising the temperature, by lowering the pressure, and by feeding into it ammonia gas to lower the partial pressure of melamine in the gas phase. The gas containing ammonia and melamine is fed into a quencher, in which the melamine is crystallized. Trial runs carried out in accordance with this in a small-scale, continuous working trial process surprisingly yielded a very pure product. The purity was 99.9%, i.e. with respect to purity the product fully met the requirements of customers.

It was further observed, surprisingly, that the retention time of the melamine in the vaporizer was not of significance. In the process disclosed in patent U.S. Pat. No. 3,484,440, the retention time of the melamine melt in the vaporizer was at minimum 1 hour. Thus any impurities formed were caused to convert into melamine. In the process according to the present invention, the said retention time was throughout the trial run less than half an hour, mostly only a few minutes. The purity of the product was 99.9% at all times, regardless of the retention time. Also, substantial amounts of impurities did not accumulate in the vaporizer, since for most of the duration of the trial run its liquid content was very low and did not substantially increase.

The most important operational differences between the present invention and the process described in patent U.S. Pat. No. 3,484,440 are thus the fact that the product gas of the reactor is not directed to the vaporizer and the fact that the retention time in the vaporizer may be less than half an hour. The most important advantages over the said process are the product purity 99.9% (separate purification is not required) and the fact that the offgases are obtained at a high pressure (approx. 100 bar).

Figure 2A:
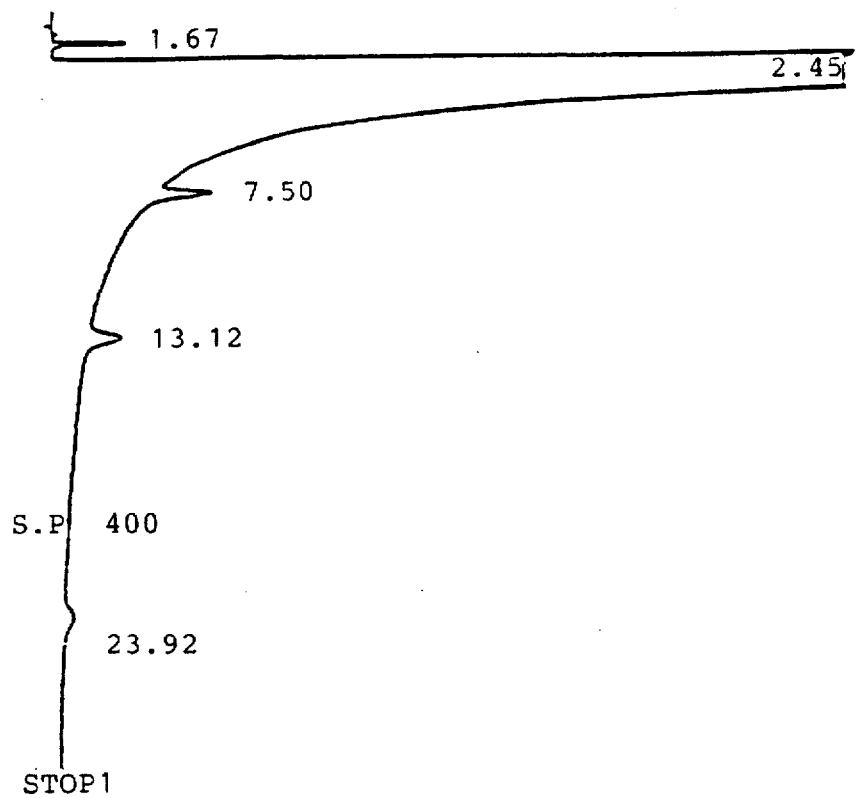
Figure 2B:
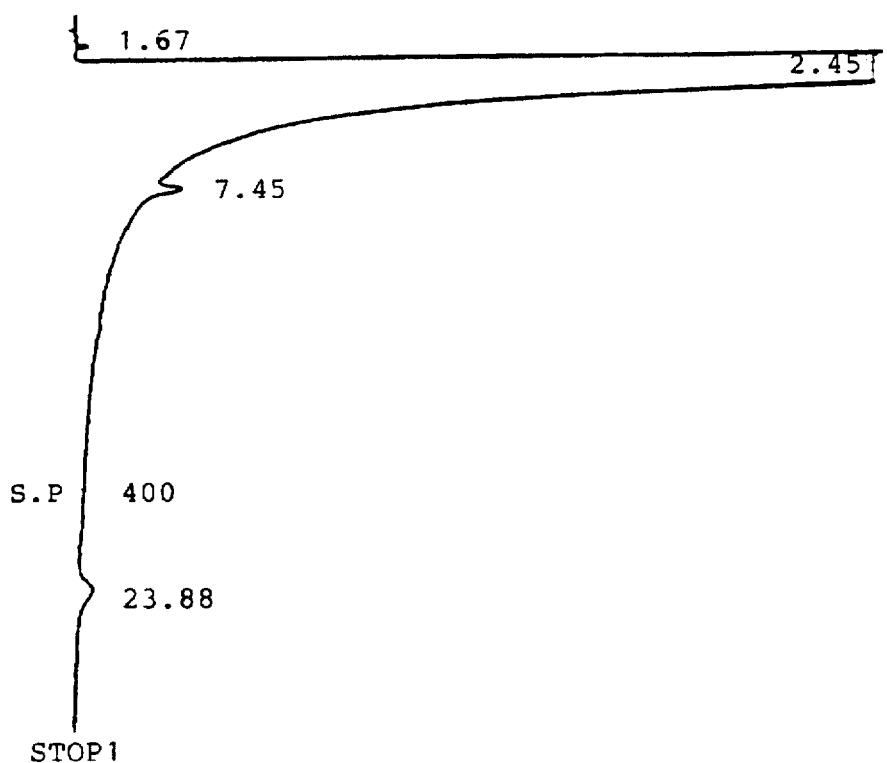
Figure 3A:
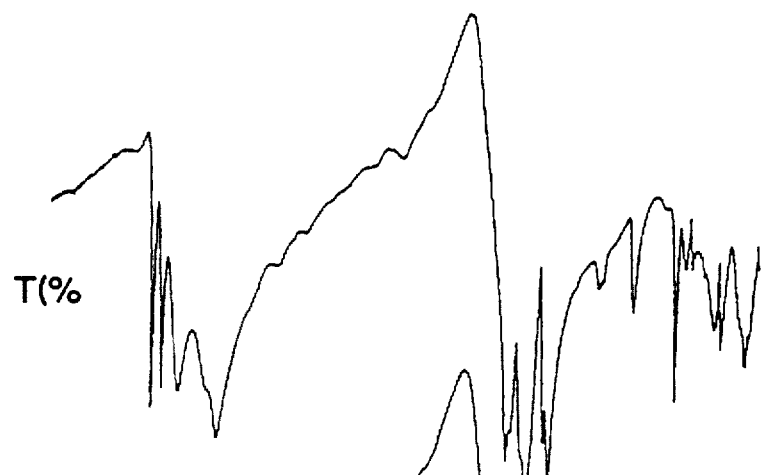
Figure 3B:
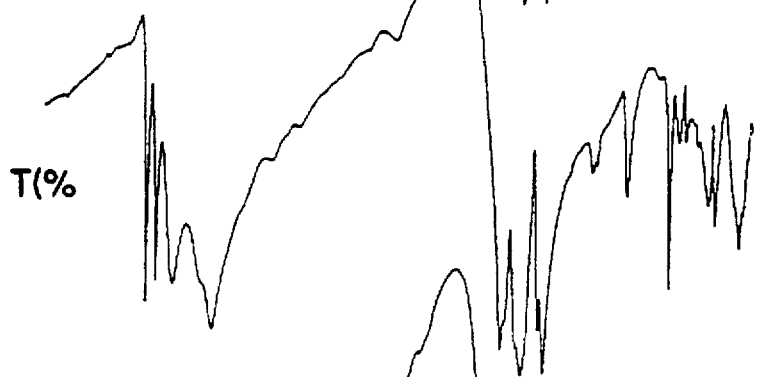
Figure 3C:
Figure 4A:
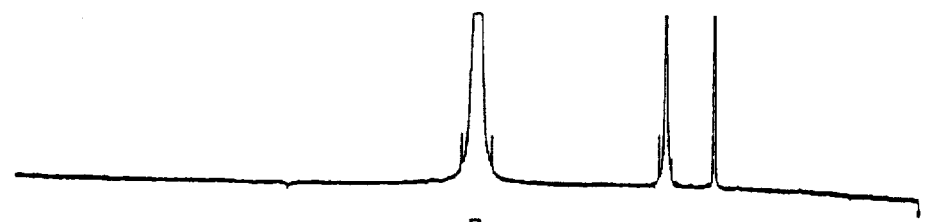
Figure 4B:
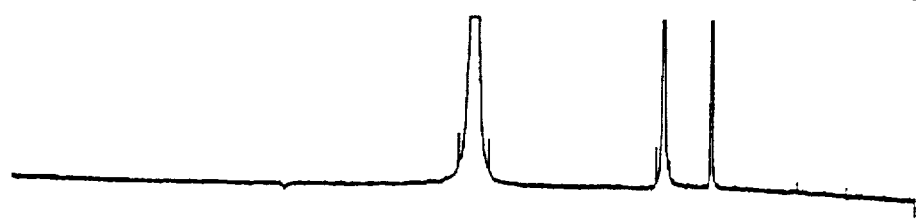
Figure 4C:
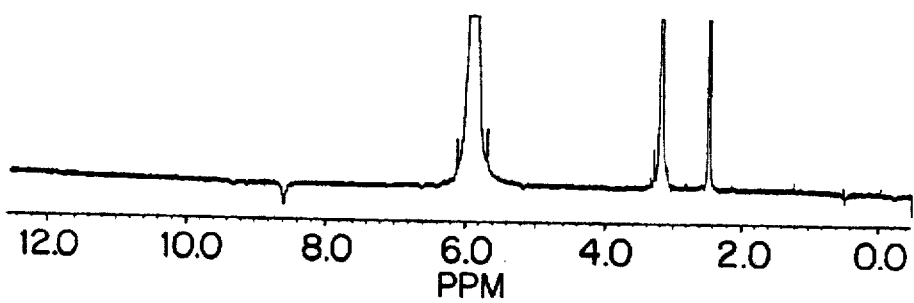
Figure 5A:
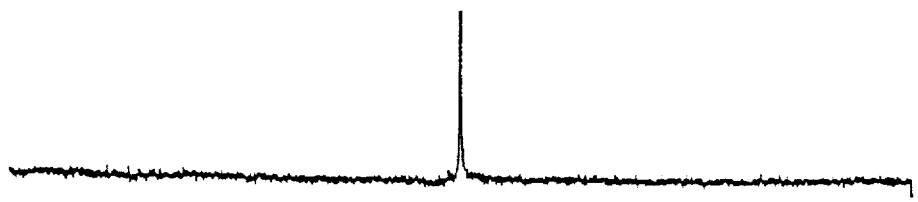
Figure 5B:
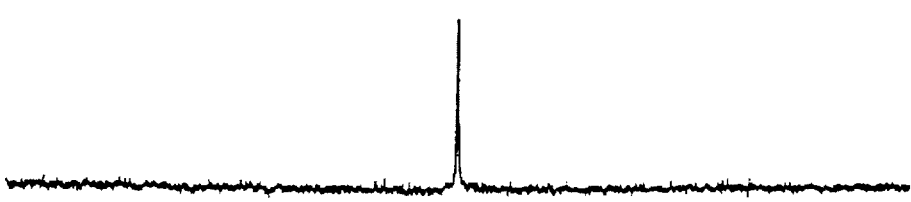
Figure 5C:
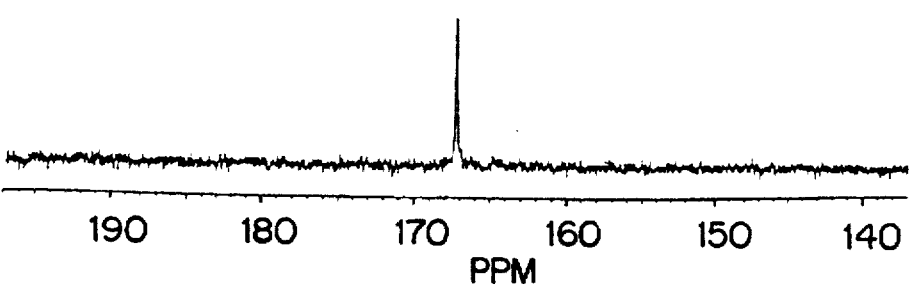

The invention is described below in greater detail, with reference to the accompanying drawings, in which FIG. 1 depicts a process diagram of a system which can be used for implementing the process according to the invention, FIG. 2 depicts LC chromatograms of a melamine prepared according to the invention and of a commercial melamine, FIG. 3 depicts IR spectra of a melamine prepared according to the invention and of two commercial melamines, FIG. 4 depicts $^1$H-NMR spectra of a melamine prepared according to the invention and of two commercial melamines, and FIG. 5 depicts $^{13}$C-NMR spectra of a melamine prepared according to the invention and of two commercial melamines.

In accordance with FIG. 1, urea melt and ammonia at approx. 400° C. are fed into a reactor 1 via the same pipe connection. The conditions prevailing in the reactor are those of a typical high-pressure process, i.e. the temperature is 360°–430° C. and the pressure within the range 50–150 bar. The heating is by internal heating elements. The gas mixture obtained from the reactor is separated from the melamine melt and is directed for further treatment. The further treatment may be, for example, a scrub with molten urea, whereby the melamine present in the gas is recovered. The gas is obtained at a pressure almost equal to the reactor pressure. The melamine melt is directed to a vaporizer 2. Thus carbon dioxide will not enter the vaporizer, except in a minute amount dissolved in melamine. In the vaporizer the temperature is within the range 420°–470° C. and the pressure within the range 20–90 bar. The heating of the vaporizer is implemented by using, for example, internal heating elements. Ammonia is fed into the vaporizer at minimum at such an amount that all of the melamine will vaporize. For example, when the pressure is 50 bar and the temperature 450° C., at minimum approx. 2.4 kg of ammonia per one kilogram of melamine is needed in the vaporizer. The retention time of the melamine melt in the vaporizer is typically less than half an hour. The gas mixture containing melamine and ammonia is directed from the vaporizer to a quencher 3. Simultaneously a cooling liquid, which may be, for example, water or ammonia, is injected into the quencher. The cooling liquid, when vaporizing, will bind the heat released in the cooling and crystallization of the melamine. The ammonia gas discharges from the upper section of the quencher together with the vaporized cooling liquid. Any unvaporized portion of the cooling liquid will be discharged from the bottom of the quencher together with the melamine crystals. The quencher pressure and temperature are dependent on the cooling liquid used. Preferably, however, the temperature is below 130° C. and the pressure below 40 bar. The vaporized cooling liquid leaving the quencher is separated from the ammonia. The condensed ammonia is recycled for use. Of course, if ammonia is used as the cooling liquid, the last-mentioned separation need not be carried out. The melamine discharged from the bottom is dried. Further purification is not necessary; the product as such fulfills the purity requirements.

The process according to the invention was tested in several continuous-working trial runs by using a testing apparatus having a maximum capacity of approx. 6 kg of melamine per hour. One of the trial runs is described in the following example.

EXAMPLE

Urea melt was fed into the reactor at a rate of 5.2 kg/h and hot (400° C.) ammonia at a rate of 2.7 kg/h. The pressure in the reactor was 100 bar, the temperature being 400° C. For heating, internal electric heating elements were used, at the start-up stage also external electric band heaters. The reactor offgas contained melamine 0.90% and carbon dioxide 14.9%, the balance being ammonia The offgas melamine was not recycled into the process, even though it was recovered by water cooling. Melamine melt was obtained from the reactor at a rate of 1.49 kg/h, and it was directed to the vaporizer. Ammonia having a temperature of 400° C.

was also fed into the reactor, at a rate of 6.3 kg/h. By means of the electric heater the vaporizer was maintained at the temperature of 450° C. the pressure being 50 bar. The retention time of liquid melamine was at all times less than half an hour, in general only a few minutes. The retention time could be noted by observing the vaporizer surface level measurement. A gas mixture which contained melamine 3.1 mol-%, the balance being ammonia, was obtained from the vaporizer. This gas mixture flowed into the quencher, into which water was injected. The quencher pressure was 2 bar (abs) and temperature 120° C. Practically all of the melamine fed into the quencher was recovered therefrom in crystalline form. The purity of the product was 99.9%.

FIGS. 2–5 show analysis results in which the melamine product obtained in the trial run described above, product (c), is compared with commercial melamine products of two different manufacturers, product (a) and product (b), meeting the general purity requirements. The said analysis results are LC chromatograms (FIG. 2), FTIR spectra (FIG. 3), $^1$H-NMR spectra (FIG. 4) and $^{13}$C-NMR spectra (FIG. 5). These, together with other analysis data, indicate that the melamine product obtained in the trial run is at least as pure as the commercial products available on the market, and that its purity is 99.9%.

We claim:

1. A process for the preparation of melamine from urea, which comprises:
   (a) feeding molten urea and hot ammonia gas into a reactor having a pressure within the range 50–150 bar and a temperature within the range 360°–430° C., whereby a reaction product is obtained which contains a liquid melamine melt and an offgas,
   (b) separating said offgas from the liquid melamine melt,
   (c) directing the liquid melamine melt thus obtained to a vaporizer,
   (d) vaporizing the liquid melamine melt in the vaporizer, whereby a melamine-containing gas is produced, and
   (e) rapidly cooling the melamine-containing gas obtained from the vaporizer, whereby the melamine is crystallized in a very pure state.

2. The process according to claim 1, wherein the melamine has a purity of at minimum 99.9%.

3. The process according to claim 1, wherein the step of vaporizing the melamine in the vaporizer is carried out by lowering the pressure.

4. The process according to claim 1, wherein the vaporizer retains the melamine for less than half an hour during the vaporizing step.

5. The process according to claim 1, wherein the step of cooling the melamine-containing gas is carried out by contacting it directly with a liquid cooling agent, the temperature being below 130° C. and the pressure below 40 bar.

6. The process according to claim 5, wherein said cooling agent is ammonia or water.

7. The process according to claim 4, wherein the vaporizer retains the melamine for less than 10 minutes during the vaporizing step.

8. The process according to claim 1, wherein the step of vaporizing the melamine in the vaporizer is carried out by raising the temperature.

9. The process according to claim 1, wherein the step of vaporizing the melamine in the vaporizer is carried out by feeding ammonia gas into the vaporizer.

10. A process for the preparation of melamine from urea which comprises:
    (a) feeding molten urea and hot ammonia gas into a reactor having a pressure within the range 50–150 bar and a temperature within the range 360°–430° C., whereby a reaction product is obtained which contains a liquid melamine melt and an offgas,
    (b) separating said offgas from the liquid melamine melt,
    (c) directing the liquid melamine melt thus obtained to a vaporizer,
    (d) vaporizing the liquid melamine melt in the vaporizer, whereby a melamine-containing gas is produced, and
    (e) rapidly cooling the melamine-containing gas obtained from the vaporizer, whereby the melamine is crystallized and the crystallized melamine has a purity of at minimum 99.9%.

11. The process according to claim 10, wherein the step of vaporizing the melamine in the vaporizer is carried out by lowering the pressure.

12. The process according to claim 10, wherein the step of vaporizing the melamine in the vaporizer is carried out by raising the temperature.

13. The process according to claim 10, wherein the step of vaporizing the melamine in the vaporizer is carried out by feeding ammonia gas into the vaporizer.

14. The process according to claim 10, wherein the vaporizer retains the melamine for less than half an hour during the vaporizing step.

15. The process according to claim 14, wherein the vaporizer retains the melamine for less than 10 minutes during the vaporizing step.

16. The process according to claim 10, wherein the step of cooling the melamine-containing gas is carried out by contacting it directly with a liquid cooling agent, the temperature being below 130° C. and the pressure below 40 bar.

17. The process according to claim 16, wherein said cooling agent is ammonia or water.

18. A process for the preparation of melamine from urea which comprises:
    (a) feeding molten urea and hot ammonia gas into a reactor having a pressure within the range 50–150 bar and a temperature within the range 360°–430° C., whereby a reaction product is obtained which contains a liquid melamine melt and an offgas,
    (b) separating said offgas from the liquid melamine melt,
    (c) directing the liquid melamine melt thus obtained to a vaporizer,
    (d) retaining the liquid melamine melt in the vaporizer for less than 10 minutes, whereby a melamine-containing gas is produced, and
    (e) cooling the melamine-containing gas obtained from the vaporizer by contacting it directly with ammonia or water, the temperature being below 130° C. and the pressure below 40 bar, whereby the melamine is crystallized and the crystallized melamine has a purity of at minimum 99.9%.

* * * * *